US011826160B2

(12) United States Patent
Na et al.

(10) Patent No.: US 11,826,160 B2
(45) Date of Patent: Nov. 28, 2023

(54) NERVE DISORDER DIAGNOSIS APPARATUS AND METHOD USING VIRTUAL REALITY

(71) Applicant: Samsung Life Public Welfare Foundation, Seoul (KR)

(72) Inventors: Duk Lyul Na, Seoul (KR); Ko Woon Kim, Seoul (KR); Ju Hee Chin, Seongnam-si (KR); Byung Hwa Lee, Anyang-si (KR); Jong Doo Choi, Seoul (KR); Jee Hyun Choi, Seoul (KR); Hio Been Han, Gimpo-si (KR)

(73) Assignee: Samsung Life Public Welfare Foundation, Seoul (KR)

( * ) Notice: Subject to any disclaimer, the term of this patent is extended or adjusted under 35 U.S.C. 154(b) by 522 days.

(21) Appl. No.: 16/496,100

(22) PCT Filed: Mar. 20, 2018

(86) PCT No.: PCT/KR2018/003203
§ 371 (c)(1),
(2) Date: Sep. 20, 2019

(87) PCT Pub. No.: WO2018/174507
PCT Pub. Date: Sep. 27, 2018

(65) Prior Publication Data
US 2020/0093414 A1 Mar. 26, 2020

(30) Foreign Application Priority Data
Mar. 23, 2017 (KR) .................. 10-2017-0037050

(51) Int. Cl.
*A61B 5/00* (2006.01)
*G16H 50/20* (2018.01)
*G06F 3/01* (2006.01)

(52) U.S. Cl.
CPC ............ *A61B 5/4088* (2013.01); *G06F 3/013* (2013.01); *G16H 50/20* (2018.01)

(58) Field of Classification Search
CPC ......... A61B 5/4088; A61B 5/00; A61B 5/744; G06F 3/013; G16H 50/20; G16H 40/63; G06Q 50/22
See application file for complete search history.

(56) References Cited

U.S. PATENT DOCUMENTS

2008/0280276 A1 11/2008 Raber et al.
2012/0022343 A1 1/2012 Shastri et al.
(Continued)

FOREIGN PATENT DOCUMENTS

KR 10-2002-0092944 A 12/2002
KR 10-2008-0084873 A 9/2008
(Continued)

OTHER PUBLICATIONS

L. Lhotska, O. Stepankova, P. Novak, J. Dolezal, J. Havlikand M. Uller, "Student projects in assistive technologies," 2014 Information Technology Based Higher Education and Training (ITHET), 2014, pp. 1-8, doi: 10.1109/ITHET.2014.7155706. (Year: 2014).*

*Primary Examiner* — Patrick Fernandes
*Assistant Examiner* — Joseph A Tombers
(74) *Attorney, Agent, or Firm* — Rabin & Berdo, P.C.

(57) ABSTRACT

The purpose of the present invention is to diagnose a neurological disease such as dementia by using virtual reality, and the present invention receives a neurological disease-diagnosing problem from an external device, displays a virtual reality image through a display on the basis of the received neurological disease-diagnosing problem, and performs an examination using the virtual reality image according to user actions detected through various sensors. This process can be performed when linked with an external device such as a PC or a smart phone. Particularly, with (Continued)

respect to the neurological disease-diagnosing problem, the present invention includes: a first screen for introducing at least one object in a virtual reality space and hiding the same; and a second screen having a question on the hidden object. According to the present invention, neurological disease such as dementia can be conveniently examined without inconveniencing or burdening a patient.

20 Claims, 18 Drawing Sheets

(56) References Cited

U.S. PATENT DOCUMENTS

| | | | | |
|---|---|---|---|---|
| 2012/0190968 | A1* | 7/2012 | Raber | A61B 5/4088 |
| | | | | 600/411 |
| 2014/0315169 | A1* | 10/2014 | Bohbot | G16H 30/20 |
| | | | | 434/236 |
| 2016/0034032 | A1* | 2/2016 | Jeong | G02B 27/0093 |
| | | | | 345/156 |
| 2016/0125748 | A1 | 5/2016 | Ashford | |
| 2016/0351069 | A1* | 12/2016 | Faubert | G09B 19/00 |
| 2017/0173262 | A1* | 6/2017 | Veltz | G16H 20/17 |

FOREIGN PATENT DOCUMENTS

| | | |
|---|---|---|
| KR | 10-2014-0046629 A | 4/2014 |
| KR | 10-2014-0134417 A | 11/2014 |

* cited by examiner (a)  (b)  (c)

| Test institute | Department of neuropsychiatry | Tester name | jin-su Kim professor |
|---|---|---|---|
| Patient name | Kil-dong Hong | Date of birth | 2017-01-06 |
| Administrator | Kil-dong Hong | Treatment receipt date | 2017-01-06 |
| Receipt number | PH2017103-A-1 | Sex | ⌄ |
| Test time | 90:34:24 AM | Nationality | ⌄ |

| | | | |
|---|---|---|---|
| ☑ | Apple | ☐ | Cellular phone |
| ☑ | Glasses | ☐ | Remote controller |
| ☐ | Table clock | ☑ | Gloves |
| ☐ | Teddy bear | ☑ | Wallet |
| ☐ | Camera | | |

Fig. 23

| Number of times | 1 | 2 | 3 | 4 | 5 | 6 | 7 | 8 | 9 | 10 | 11 | 12 | Total | | |
|---|---|---|---|---|---|---|---|---|---|---|---|---|---|---|---|
| Item | Apple | Banana | Wallet | Money | Apple | Banana | Wallet | Money | Apple | Banana | Wallet | Money | Correct answers | Incorrect answers | Ratio of correct answers |
| Telling hidden items | o | o | | | o | o | | | o | o | | | 4 | 8 | 80% |
| Jigsaw puzzle of hidden items | o | o | | | | o | | | | o | o | | 7 | 5 | 30% |
| Finding places | o | | o | x | o | | o | x | o | | o | x | 7 | 5 | 30% |
| Finding items | o | | | o | o | | | o | o | | | o | 6 | 6 | 50% |
| Time for finding hidden items (seconds) | 23 | | | 23 | 23 | | | 26 | 45 | | | 67 | Total consumption time | 123 | |
| Distance for finding hidden items (cm) | 123 | | | 23 | 45 | | | 345 | 3456 | | | 98 | Total distance | 123 | |

| Number of times | Future memory | Correct answers | Consumed time (seconds) |
|---|---|---|---|
| 1 | Turning off induction | o | 111 |

[< Previous step]   [Finish the test after storing a test result.]   [Finish the test.]

NERVE DISORDER DIAGNOSIS APPARATUS AND METHOD USING VIRTUAL REALITY

TECHNICAL FIELD

The present invention relates to an apparatus and method for diagnosing a neurological disorder, which can diagnose a neurological disorder such as dementia or the like using virtual reality so that the diagnosis can be conveniently performed without giving a user mental stress.

BACKGROUND ART

Aging is rapidly progressed around the world, and the number of dementia patients also increases according thereto. Accordingly, financial cost for managing and treating the dementia patients increases. Recently, medicines for delaying and improving manifestation of dementia symptoms are developed, and investments and efforts for developing medicines with further improved effect are continued. However, since the medicines are effective only when they are used in the early stage of dementia, early diagnosis and treatment of the dementia is important.

A dementia diagnosis method through a psychological interview is generally conducted to diagnosis dementia. However, since the dementia diagnosis method through a psychological interview needs a long-time interview in a doctor's office environment, this may give a patient mental pressure or stress and lower the accuracy of the test.

As other methods for diagnosing dementia, there are a method of diagnosing a degree of dementia progress by taking brain images using MRI equipment or the like, a bio-marker method for diagnosing a degree of dementia progress by analyzing blood or cerebrospinal fluid taken from a dementia patient, and a method of diagnosing dementia by measuring brainwaves (EEG or MEG).

However, since these methods use expensive equipment, the burden of cost increases, and since blood or cerebrospinal fluid of a dementia patient should be taken, it is accompanied with pains of the patient.

DISCLOSURE OF INVENTION

Technical Problem

Therefore, the present invention has been made in view of the above problems, and it is an object of the present invention to easily diagnose a neurological disorder such as dementia or like using a computer and virtual reality equipment and reduce inconvenience and mental stress of a user generated in the process of diagnosing a neurological disorder.

Technical Solution

To accomplish the above object, a virtual reality apparatus according to the present invention provides a virtual reality environment based on an image and includes: a display for displaying the image; a sensing unit for sensing motions of a user; a communication unit for communicating with an external device; and a control unit for displaying a virtual reality image on the display on the basis of questions for diagnosing a neurological disorder received from the external device through the communication unit, and progressing a test for diagnosing the neurological disorder while sensing motions of the user through the sensing unit.

At this point, the questions for diagnosing a neurological disorder is configured to include: a first screen for hiding at least an item in a virtual reality space after introducing the item; and a second screen including questions on the at least an item.

The first screen may be configured such that an avatar appears and hides the at least an item in a specific space or specific furniture.

The background images of the first screen and the second screen may be configured to be the same as a home interior environment in which the user lives.

The questions for diagnosing a neurological disorder may be classified into questions having any one level of difficulty among a plurality of levels of difficulty, and it may be configured to increase the number of hidden items as the level of difficulty increases.

The second screen may be configured to perform at least one or more of: a recall step of diagnosing whether a user remembers a hidden item; a recognition step of diagnosing whether the user distinguishes between the hidden item and the other items; and a matching step of diagnosing whether the user can associate a hidden item with a location.

The second screen performing the recall step may sequentially display the hidden items and include a first user interface for inquiring the user to say where the displayed items are hidden.

The second screen performing the recognition step may display a package screen in which the hidden items and new items not introduced before are mixed and include a second user interface for inquiring the user to distinguish between the hidden items and the new items in the package screen.

The second screen performing the matching step may display a virtual reality space in which the at least an item is hidden and include a third user interface for asking the user to find the hidden items while the user himself or herself moves.

The control unit may include a result processing module for calculating a score on the basis of a first condition of a distance that the user has moved, a second condition of a time consumed by the user to answer all the questions for diagnosing a neurological disorder, and a third condition of an answer sheet created on the basis of a voice or a motion of the user.

The result processing module may calculate the score by assigning a preset weighting value to each of the first to third conditions.

In addition, the control unit may compare the calculated score with a reference score and determine the second user as normal if the calculated score is equal to or higher than the reference score.

According to another aspect of the present invention, a method of driving a virtual reality apparatus for providing a user with a virtual reality environment based on an image may include the steps of: receiving questions for diagnosing a neurological disorder from an external device; displaying a virtual reality image through a display on the basis of questions for diagnosing a neurological disorder, and progressing a test using the virtual reality image according to a motion of the user sensed through a sensing unit; and transmitting information related to the test progressed using the virtual reality image to the external device.

At this point, the step of displaying a virtual reality image may include the steps of: displaying a first screen for hiding at least an item in a virtual reality space after introducing the item; and displaying a second screen including questions on the at least an item.

Advantageous Effects

According to the present invention, a test on a neurological disorder such as dementia or the like can be easily conducted without burden by using virtual reality equipment.

Since the test can be conducted through a virtual reality environment that a user feels like a real world, not through a boring and complicated interview, and images that the user may comfortably treat, such as a home interior environment in which the user lives, are used, the mental stress can be greatly reduced by decreasing the burden of a patient.

BRIEF DESCRIPTION OF THE DRAWINGS

FIGS. 13 to 23 are views showing another example describing a method of diagnosing dementia by progressing a hide-and-find-things test using a dementia diagnosis system of the present invention.

DESCRIPTION OF SYMBOLS

Figure 1:
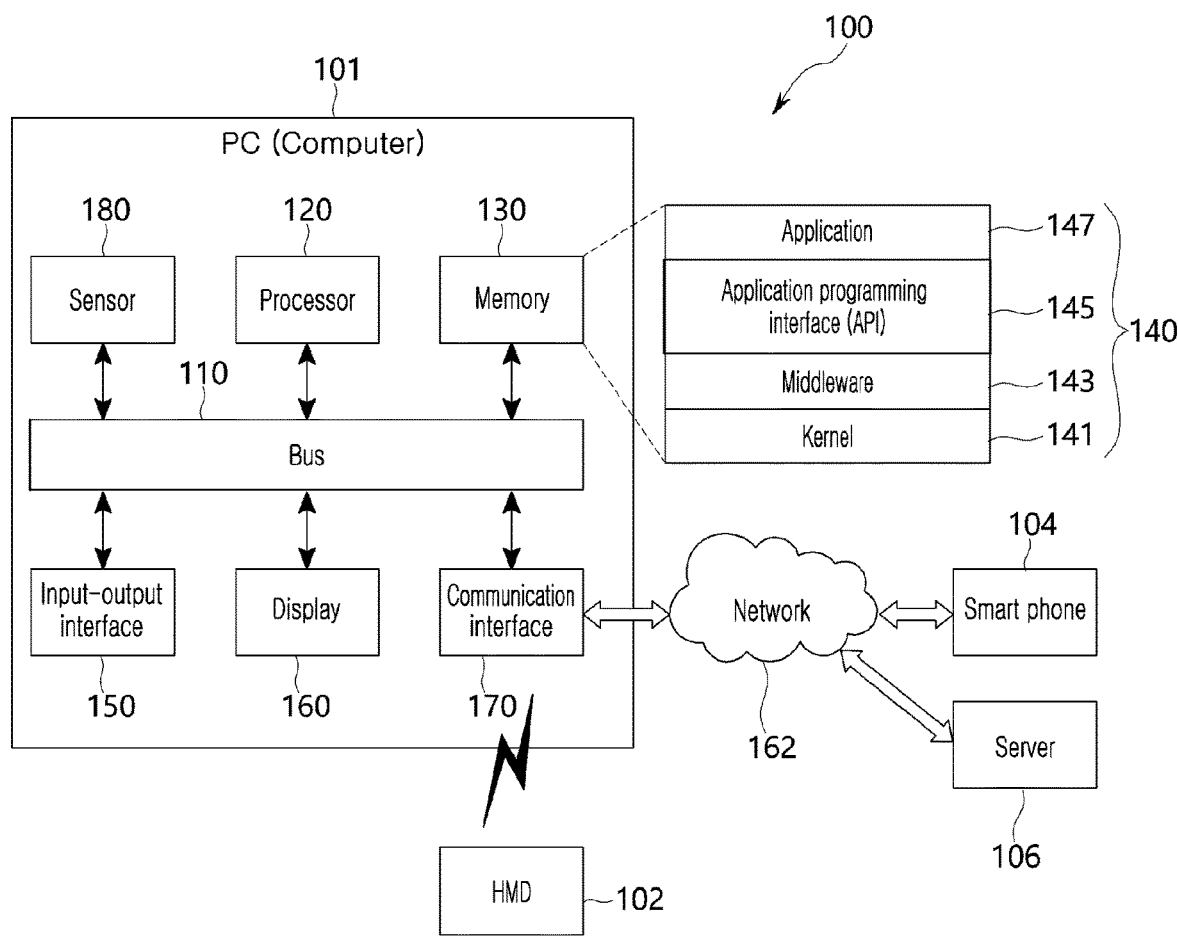
FIG. 1 is a block diagram showing the configuration of a dementia diagnosis system according to an embodiment of the present invention.

101: PC
102: Head mount display (HMD)
104: Smart phone
106: Server

BEST MODE FOR CARRYING OUT THE INVENTION

Since the present invention may make diverse changes and have various embodiments, specific embodiments will be shown in the drawings and described in detail.

As the present invention allows various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the present invention, when it is determined that the detailed description of the known art related to the present invention may obscure the gist of the present invention, the detailed description thereof will be omitted.

The terms used in the specification are used to describe only specific embodiments and are not intended to limit the present disclosure. Singular forms are intended to include plural forms unless the context clearly indicates otherwise.

It will be further understood that the terms "include", "comprise" and "have" used in this specification specify the presence of stated features, numerals, steps, operations, components, parts, or a combination thereof, but do not preclude the presence or addition of one or more other features, numerals, steps, operations, components, parts, or a combination thereof.

The terms such as "first" and "second" can be used in describing various elements, but the above elements shall not be restricted to the above terms. The above terms are used only to distinguish one element from the other.

In this specification, the "neurological disorder" means a neurodegenerative disorder, and for example, it may be selected from a group including Alzheimer's disease (AD), vessel disease dementia, frontotemporal dementia (FTD), Corticobasal degeneration (CBD), progressive supranuclear palsy (PSP), Dementia with Lewy bodies, tangle-predominant senile dementia, Pick's disease (PiD), argyrophilic grain disease, Amyotrophic Lateral Sclerosis (ALS), other motor neuron diseases, Guam parkinsonism-dementia complex, FTDP-17, Lytico-Bodig disease, multiple sclerosis, Traumatic Brain Injury (TBI), and Parkinson's disease.

FIG. 1 is a block diagram showing the configuration of a dementia diagnosis system according to an embodiment of the present invention, and a dementia diagnosis system 100 may include a PC (computer) 101, a virtual reality apparatus 102, a network 162, a smart phone 104, and a server 106.

The virtual reality apparatus 102 may be a display device which can be mounted on the head of a user and directly display an image in front of the eyes of the user. For example, the virtual reality apparatus 102 may be configured of wearable glasses or a head mount display (HMD). In the example shown in the figure, the virtual reality apparatus is expressed as a HMD 102 for the convenience of explanation. The virtual reality apparatus 102 may have a form of glasses and is provided with a transparent display or an opaque display. Accordingly, the virtual reality apparatus 102 may allow a user wearing the apparatus to recognize staying in a virtual reality space.

According to an embodiment, the virtual reality apparatus 102 may further include a speaker, a microphone, a motion sensing sensor and the like, in addition to the display for giving the user a virtual reality experience. The virtual reality apparatus 102 like this will be described in detail with reference to FIG. 3.

The PC 101 may include a bus 110, a processor 120, a memory 130, an input-output interface 150, a display 160, and a communication interface 170. The bus 110 connects constitutional components 110 to 170 with each other and may include a circuit for transferring communications (e.g., control messages or data) between the constitutional components. The processor 120 may include one or more among a central processing unit, an application processor and a communication processor.

The processor 120 may execute an operation or process data related to control and/or communication of at least one of the other constitutional components of the PC 101.

The memory 130 may include volatile and/or nonvolatile memory. The memory 130 may store commands or data related to at least one of the other constitutional components of the PC 101 and store software and/or programs 140.

The program 140 may include a kernel 141, middleware 143, an application programming interface (API) 145, and an application 147, and at least some of the kernel 141, the middleware 143 and the API 145 may be referred to as an operation system.

The input-output interface 150 may transfer a command or data inputted from a user or another external device to the other constitutional components of the PC 101 or output a command or data received from the other constitutional components of the PC 101 to the user or another external device.

The display 160 may include a liquid crystal display (LCD), a light emitting diode (LED) display, an organic LED (OLED) display and the like. The display 160 may include a touch screen and receive a touch, a gesture, an approach or a hovering input using an electronic pen or a part of the body of the user.

The communication interface 170 allows the PC 101 to communicate with external devices such as the virtual reality apparatus 102, the smart phone 104, the server 106 and the like through various wireless communications or wired communications.

The wireless communication method may include cellular communication using at least one among LTE, LTE Advance (LTE-A), code division multiple access (CDMA), WCDMA (wideband CDMA), universal mobile telecommunications system (UMTS), Wireless Broadband (WiBro), and Global System for Mobile Communications (GSM) and may include short distance communication. The short distance communication may include at least one among wireless fidelity (WiFi), Bluetooth, Bluetooth low energy (BLE), Zigbee, and near field communication (NFC).

The wired communication method may include at least one among universal serial bus (USB), high definition multimedia interface (HDMI), recommended standard-232 (RS-232), power line communication, and plain old telephone service (POTS).

The network 162 may include a telecommunication network, for example, a computer network (e.g., LAN or WAN), Internet, a telephone network or the like.

All or some of the operations executed in the PC 101 may be executed in association with the smart phone 104 or the server 106.

According to an embodiment, when the PC 101 performs a function or a service automatically or on demand, the PC 101 may request the smart phone 104 or the server 106 to perform at least part of the function related thereto, instead of autonomously performing or in addition to the function or the service. Then, the smart phone 104 or the server 106 may perform the requested function or an additional function and transfer a result thereof to the PC 101.

The PC 101 may provide the requested function or service using the received result as is or additionally processing the result. To this end, cloud computing, distributed computing or client-server computing techniques may be used in the system of the present invention.

Figure 2:
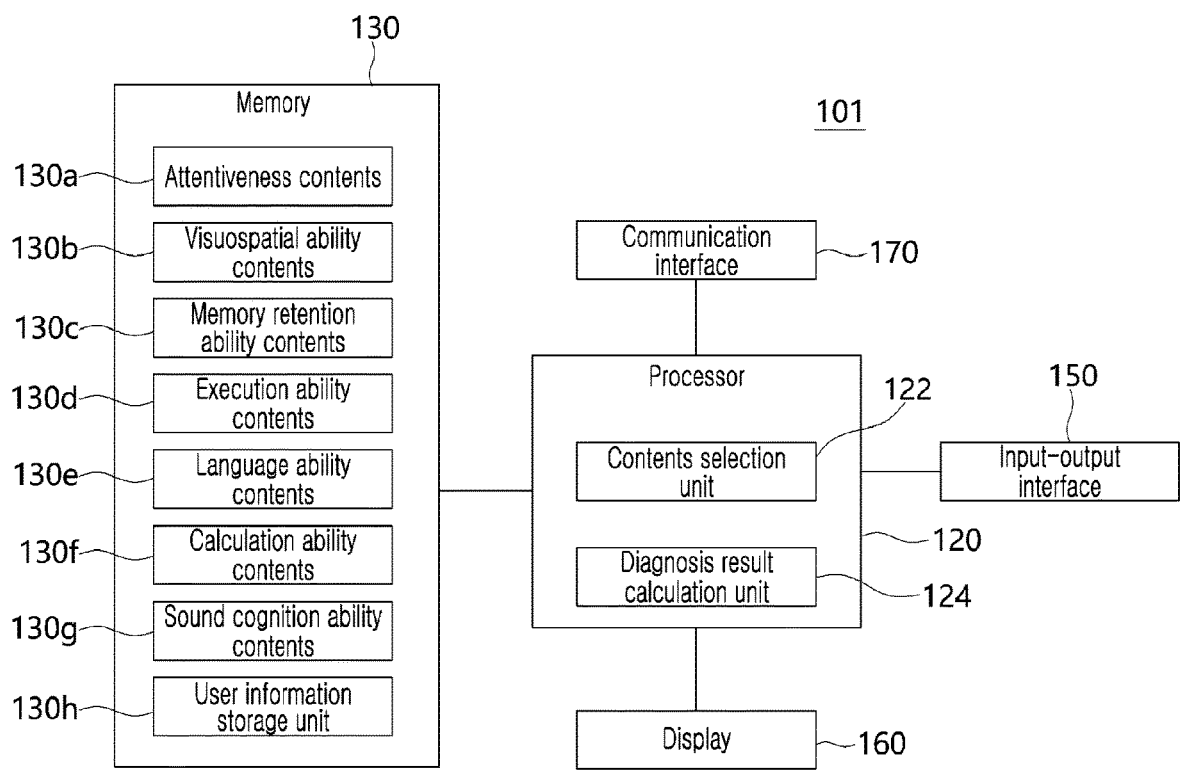
FIG. 2 is a block diagram showing the configuration of a PC according to an embodiment of the present invention.

FIG. 2 is a block diagram showing the configuration of a PC according to an embodiment of the present invention and may include a processor 120, a memory 130, a communication interface 170, a display 180, and an input-output interface 150.

The processor 120 may include a contents selection unit 122 and a diagnosis result calculation unit 124. The contents selection unit 122 may receive information on a second user from a first user through the input-output interface 150 and select questions based on any one among the contents stored in the memory 130.

Here, the first user is a professional personnel who progresses a dementia test and may be a person who determines dementia of the second user, for example, a doctor or a nurse as a tester.

The second user is a subject of a dementia test and may be a testee who visits a hospital and takes the dementia test.

The first user may select any one among the questions provided by the contents selection unit 122 so that the PC 101 may transmit the selected question to the virtual reality apparatus 102.

That is, the PC 101 may receive information for selecting at least a piece of the contents or information for selecting a question mapped to at least a piece of the contents and transmit questions for testing to the virtual reality apparatus 102 on the basis of the received information.

According to an embodiment, the contents selection unit 122 may refer to examination records of the second user with reference to a user information storage unit of the memory 130 and automatically select and recommend contents on the basis of the referred result. For example, the contents selection unit 122 may refer to the examination records of the second user and inform the first user of contents the same as or similar to the contents for dementia test conducted before, through the display 160.

According to an embodiment, after the PC 101 transmits the questions for dementia test to the virtual reality apparatus 102, the contents selection unit 122 may readjust the type and level of difficulty of the questions for dementia test on the basis of an interrupt received from the virtual reality apparatus 102 and transmit the readjusted questions for dementia test to the virtual reality apparatus 102.

Here, the interrupt received from the virtual reality apparatus 102 may be created by the virtual reality apparatus 102 when a dementia test result of the second user through the virtual reality apparatus 102 is lower than a threshold value. For example, when the score of the dementia test result of the second user is less than 50 points out of 100 points, the virtual reality apparatus 102 may create an interrupt and transmit the interrupt to the PC 101.

Like this, when the score of the dementia test result of the second user is extremely low as the level of difficulty of the initially transmitted questions for dementia test is inappropriate, the virtual reality apparatus 102 transmits an interrupt so that the second user may answer questions of a proper level of difficulty. Accordingly, the present invention may diagnose dementia more correctly and may be helpful to improving brain functions by performing brain training step by step when a dementia patient uses the apparatus.

The diagnosis result calculation unit 124 of the processor 120 may receive test result information from the virtual reality apparatus 102 and calculate a diagnosis result on the basis of the test result information. The diagnosis result calculation unit 124 may create a report on the basis of the calculated diagnosis result and output the created report through the display 160.

For example, the diagnosis result calculation unit 124 may create a marking result by comparing correct answers of the questions transmitted to the virtual reality apparatus 102 and choice alternatives selected by the second user through the virtual reality apparatus 102. For example, the marking result may be calculated on the basis of a 100-point scale. The diagnosis result calculation unit 124 may calculate a marking result for each question item and create a report on the basis of a calculation result.

Specifically, a plurality of questions transmitted from the PC 101 to the virtual reality apparatus 102 may be questions selected from at least one among attentiveness contents, visuospatial ability contents, memory retention ability contents, execution ability contents, language ability contents, calculation ability contents, and sound cognition ability contents stored in the memory 130.

For example, when the questions transmitted from the PC 101 to the virtual reality apparatus 102 are ten questions including five questions corresponding to the memory retention ability contents and five questions corresponding to the execution ability contents, the diagnosis result calculation unit 124 may separately calculate a marking result of the memory retention ability contents and a marking result of the execution ability contents. Accordingly, the present invention may separately analyze the memory retention ability and the execution ability of an examination subject, i.e., the second user taking the examination.

Meanwhile, when the dementia diagnosis of the second user is completed, the diagnosis result calculation unit 124 may store a diagnosis result in the user information storage unit 130h.

The memory 130 may include attentiveness contents 130a, visuospatial ability contents 130b, memory retention ability contents 130c, execution ability contents 130d, language ability contents 130e, calculation ability contents 130f, sound cognition ability contents 130g, and the like.

The attentiveness contents 130a may include contents configured of questions for assessing the ability of finding the same figures or paying attention to characters.

The visuospatial ability contents 130b may include contents configured of questions for assessing the ability of perceiving things or a visually combining ability.

The memory retention ability contents 130c may include contents configured of questions for assessing the ability of remembering national flags, cards or numbers.

The execution ability contents 130d may include contents configured of questions for assessing the ability of completing or categorizing a picture and the ability of recognizing similarities.

The language ability contents 130e may include contents configured of questions for assessing the ability of filling or finding words.

The calculation ability contents 130f may include contents configured of questions for assessing the ability of performing four basic arithmetic operations.

The sound cognition ability contents 130g may include contents configured of questions for assessing the ability of finding a figure corresponding to a sound or finding figures in order of hearing.

Figure 3:
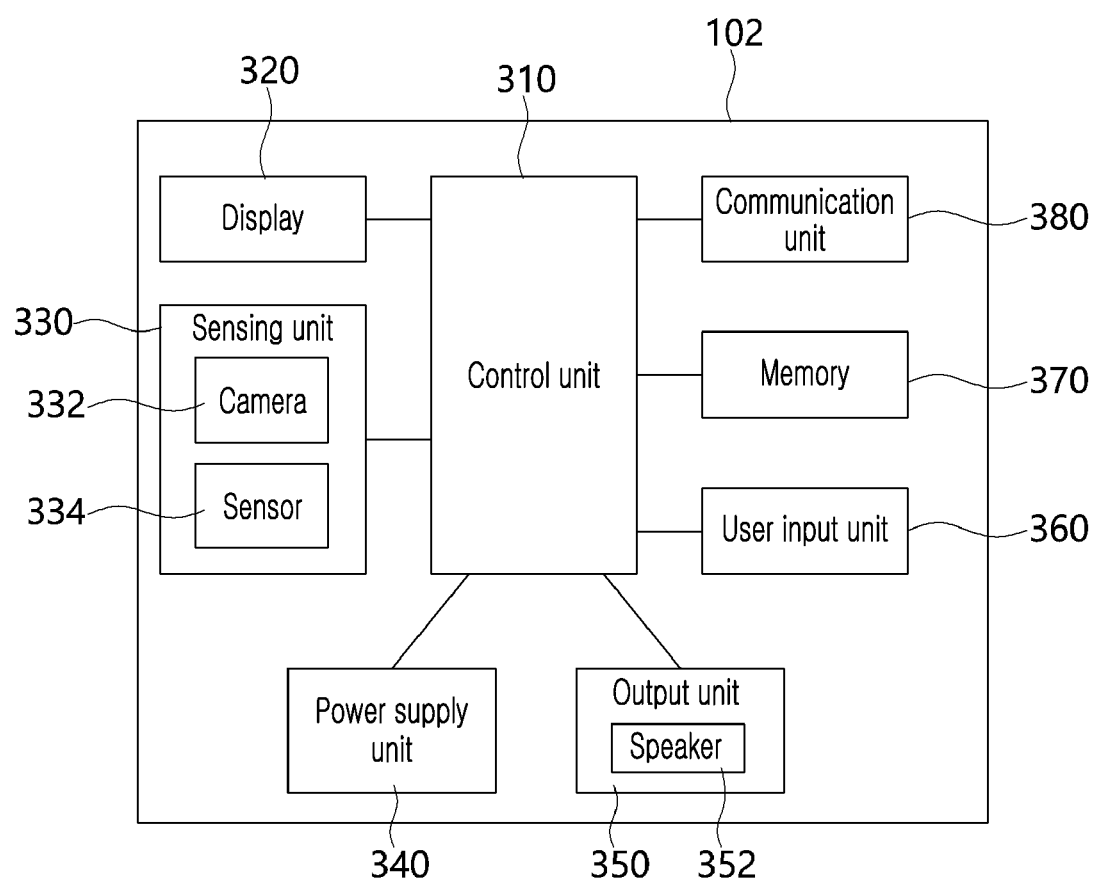
FIG. 3 is a block diagram showing the configuration of a virtual reality apparatus according to an embodiment of the present invention.

FIG. 3 is a block diagram showing the configuration of a virtual reality apparatus 102 according to an embodiment of the present invention and may include a control unit 310, a display 320, a sensing unit 330, a communication unit 380, a memory 370, a user input unit 360, a power supply unit 340, and an output unit 350.

The sensing unit 330 may include at least a camera 332 and a sensor 334.

The camera 332 photographs an object in a real space. The images of the object photographed by the camera 332 may be a moving image or continuous still images. The virtual reality apparatus 102 may be, for example, an apparatus of a glasses form provided with a communication function and a data processing function. In the virtual reality apparatus 102 worn on the second user, the camera 332 facing the front side of the second user may photograph an object in a real space.

The camera 332 may photograph at least parts of the body of the second user. For example, the camera 332 may photograph the eyes of the second user.

The virtual reality apparatus 102 may be provided with an eyeball tracking camera 332 facing the face of the second user and may track the eyeline of the second user by tracking at least one among a head pose, an eyelid, and a pupil of the second user.

In addition, the camera 332 may photograph a hand of the second user. For example, the virtual reality apparatus 102 may be provided with a hand tracking camera for tracking the hands of the second user, and the hand tracking camera may track the motion of the hand of the second user by tracking at least one among the back of the hand, a finger, a wrist or the like of the second user.

The sensor 334 may sense a state of the virtual reality apparatus 102 or a state around the virtual reality apparatus 102 and transfer sensed information. For example, the sensor 334 may acquire information on the wearing state of the second user wearing the virtual reality apparatus 102.

For example, the sensor 334 may include a geomagnetic sensor 334, an acceleration sensor 334, a gyroscope sensor 334, a proximity sensor 334, an optical sensor 334, a depth sensor 334, an infrared sensor 334, an ultrasonic sensor 334 and the like.

The communication unit 380 allows the virtual reality apparatus 102 to transmit and receive information needed to output images and adjust output images to and from the apparatuses such as the PC 101, the smart phone 104, the server 106 and the like.

The memory 370 may store information needed for the virtual reality apparatus 102 to display images 320 and to adjust the images on the basis of the slope of the virtual reality apparatus 102. The memory 379 may store information on the standard wearing state, which is a state of wearing the virtual reality apparatus 102 at a position most appropriate for the second user to be provided with images.

For example, the memory 370 may store standard wearing state information including an image of a body part of the second user acquired in the standard wearing state and feature values detected from the image of a body part acquired in the standard wearing state.

The user input unit 360 receives a user input for controlling the virtual reality apparatus 102. The user input unit 360 may receive a touch input, a key input or the like of the virtual reality apparatus 102. In addition, the user input unit 360 may also receive a gesture input of the second user photographed by the camera 332.

The power supply unit 340 supplies power needed for operation of the virtual reality apparatus 102. The power supply unit 340 may include a battery (not shown) which can charge power and may include a cable (not shown) or a cable port (not shown) for receiving power from the outside.

The output unit 350 outputs information received from the communication unit 380, processed by the control unit or stored in the memory 370 at least in a form among light, sound and vibration.

For example, the output unit 350 may include a speaker 352 for outputting audio data. In addition, the speaker 352 may output acoustic signals related to a function (e.g., a signal receiving sound, a message receiving sound, or a notification sound) performed by the virtual reality apparatus 102.

The control unit 310 may control general operation of the virtual reality apparatus 102.

For example, the control unit 310 may control the display 320, the sensing unit 330, the communication unit 380, the memory 370, the user input unit 360, the output unit 350 and the power supply unit 340 by executing programs stored in the memory 370. The control unit 310 may receive questions for diagnosing dementia by communicating with the PC 101 or the smart phone 104, store the received questions in the memory 370, and execute the questions.

The virtual reality apparatus 102 may be connected to the PC 101 or the smart phone 104 through wireless communication, short distance communication, wired communication or the like, receive information on the images related to the questions for diagnosing dementia from the PC 101 or the smart phone 104, and output the images on the display 320 of the virtual reality apparatus 102.

The control unit 310 displays a virtual reality image on the display 320 on the basis of the questions for diagnosing a neurological disorder received from an external device such as the PC 101 or the smart phone 104 and progresses a test for diagnosing the neurological disorder while sensing motions of a user through the sensing unit 330.

Various processes needed for implementation of virtual reality and the dementia test can be carried out in this process, and various information can be exchanged in association with the external device. For example, various information related to the test progressed using a virtual reality image, such as whether a user wears the virtual reality apparatus, sensed user information such as the eyeline, voice, gesture or the like of the user, answers of the second user created on the basis of the sensed information, a result of marking the answers of the second user and the like, can be transmitted to the external device in real-time or at a specific time point.

According to an embodiment, the questions for diagnosing dementia provided by the virtual reality apparatus 102 may include a first screen for hiding at least one item in a virtual reality space after introducing the item and a second screen including questions on the at least an item. Here, the background images of the first and second screens are preferably configured to be the same as the home interior environment in which the second user lives. This is to provide a conformable psychological state to a user taking a dementia test.

The first screen may be an image in which an avatar appears and hides at least an item in a specific space or specific furniture.

The second screen may be configured to perform a recall step of diagnosing whether a user remembers a hidden item, a recognition step of diagnosing whether the user distinguishes between the hidden item and the other items, and a matching step of diagnosing whether the user can associate a hidden item with a location.

At the recall step, the virtual reality apparatus 102 may sequentially display hidden items and provide a first user interface for inquiring the user to say where the displayed items are hidden.

At the recognition step, the virtual reality apparatus 102 may display a package screen in which the hidden items and new items not introduced before are mixed and provide a second user interface for inquiring the user to distinguish between the hidden items and the new items in the package screen.

At the matching step, the virtual reality apparatus 102 may display a virtual reality space in which at least an item is hidden and provide a third user interface for asking the user to find the hidden items while the user himself or herself moves.

Each of the questions for diagnosing dementia like this may be configured to have a level of difficulty among a plurality of difficulty levels, e.g., from a first level to a ninth level, and may be configured to increase the number of hidden items as the level of difficulty increases from the first level to the ninth level.

Meanwhile, when the second user completes answering the questions for diagnosing dementia, the virtual reality apparatus 102 itself may calculate a result thereof.

Specifically, the control unit of the virtual reality apparatus 102 may include a result processing module (not shown) for calculating a score on the basis of a first condition of a distance that the user has moved, a second condition of a time consumed by the user to answer all the questions for diagnosing dementia, and a third condition of an answer sheet created on the basis of a voice or a motion of the user.

At this point, the result processing module may calculate the score by assigning a preset weighting value to each of the first to third conditions.

For example, the result processing module may set a high weighting value to the first condition of the moving distance of the user, set a high weighting value to the second condition of the time consumed by the second user to answer all the questions for diagnosing dementia, or set a high weighting value to the third condition of an answer sheet created on the basis of a voice or a motion of the user.

At this point, the control unit may compare the calculated score with a reference score and determine the second user as normal if the calculated score is equal to or higher than the reference score.

The result processing module may transmit the calculated score to an external device such as the PC 101, the smart phone 104 or the like through the communication unit 380.

Figure 4:
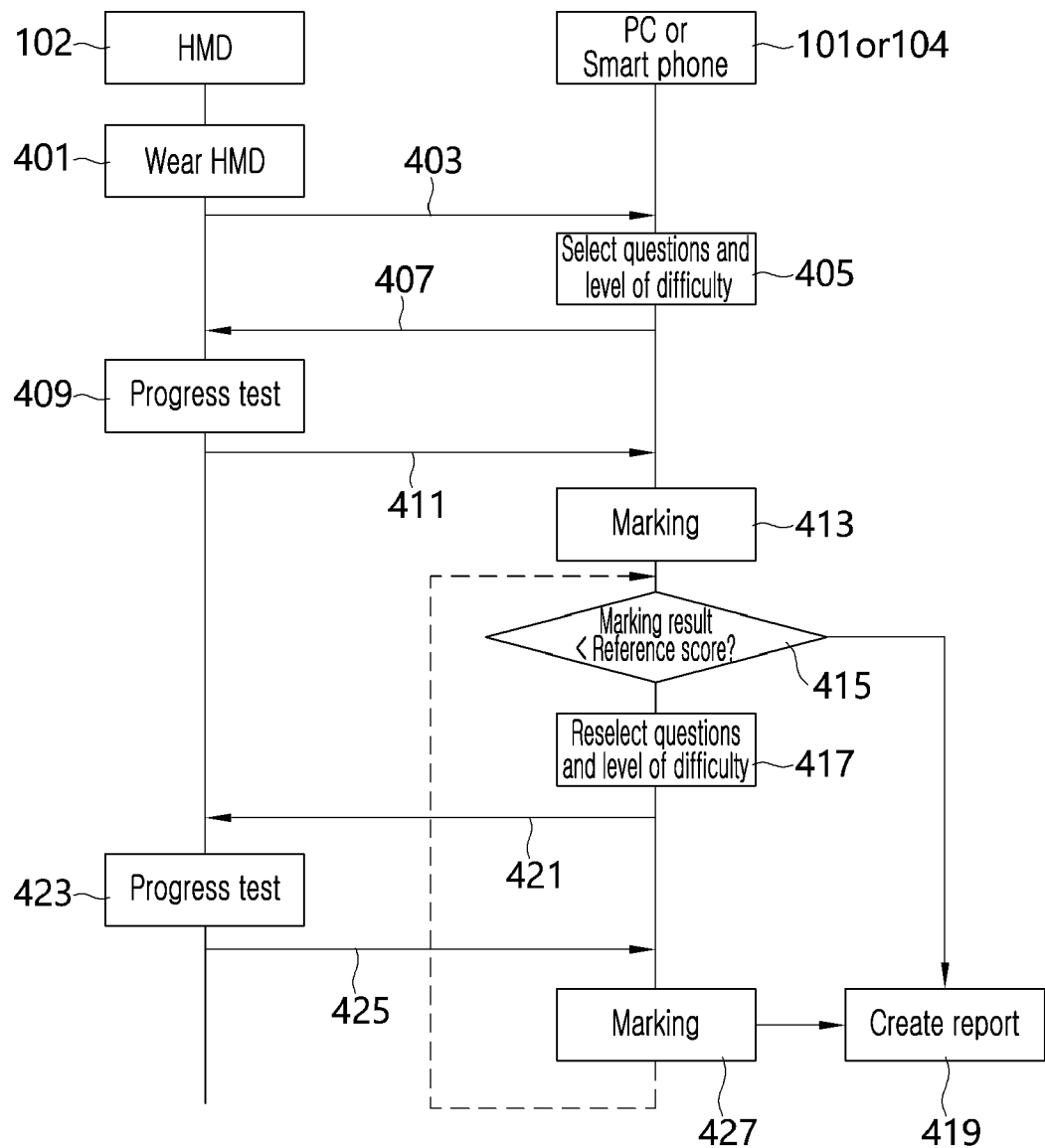
FIG. 4 is a flowchart illustrating the operation of a dementia diagnosis system according to an embodiment of the present invention.

FIG. 4 is a flowchart illustrating the operation of a dementia diagnosis system according to an embodiment of the present invention.

Although the virtual reality apparatus 102 communicates with the PC 101 or the smart phone 104 in the example as shown in the figure, it will be described assuming that the virtual reality apparatus 102 communicates with the PC 101 for the convenience explanation.

It should be noted that in the below description, the operation of communicating between the virtual reality apparatus 102 and the PC 101 may be performed between the virtual reality apparatus 102 and the smart phone 104, and at least an operation performed in the PC 101 may be performed by the smart phone 104.

The virtual reality apparatus 102 may sense whether the second user wears the virtual reality apparatus 102 (step 401). If it is sensed that that whether the second user wears the virtual reality apparatus 102, the virtual reality apparatus 102 may create a sensing signal on the basis of a sensing result and transmit the created sensing signal to the PC 101 (step 403).

The PC 101 may output a screen in response to the sensing signal received from the virtual reality apparatus 102 so that the first user may recognize that the second user wears the virtual reality apparatus 102. The PC 101 may output a user interface for requesting input of contents for diagnosing dementia of the second user in response to the sensing signal. The PC 101 may receive an input for selecting questions mapped to the contents and a level of difficulty from the first user through the user interface (step 405).

The PC 101 may transmit questions for testing and a level of difficulty to the virtual reality apparatus 102 on the basis of the information selected by the first user (step 407). For example, the questions for testing may be questions included in at least one among attentiveness contents 130*a*, visuospatial ability contents 130b, memory retention ability contents 130c, execution ability contents 130d, language ability contents 130e, calculation ability contents 130f, sound cognition ability contents 130g, and the user information storage unit 130h, which are stored in the memory of the PC 101.

The virtual reality apparatus 102 may progress a test on the basis of the questions for testing and information on the level of difficulty received from the PC 101 (step 409).

The virtual reality apparatus 102 may sense the eyeline, voice, gesture or the like of the second user using a sensor and a camera and create an answer of the second user on the basis of a sensing result. When the test is completed, the virtual reality apparatus 102 may transmit a data corresponding to the created answer to the PC 101 (step 411).

According to another embodiment, the virtual reality apparatus 102 may sense the eyeline, voice, gesture or the like of the second user and store a sensing result in a buffer by the unit of a specific time. In addition, the virtual reality apparatus 102 may transmit a signal stored in the buffer to the PC 101 in real-time.

The PC 101 may receive a data corresponding to the created answer from the virtual reality apparatus 102 and mark the answer of the second user on the basis of the received data (step 413).

The PC 101 may compare a marking result score with a reference score (step 415) and create and output a report on the basis of a compared result (step 419).

Additionally, when the marking result score is lower than the reference score, the PC 101 may output a screen requesting reselection of the questions and the level of difficulty of the questions. This is to readjust the questions and the level of difficulty to correctly diagnose dementia when the test result score of the second user is extremely low. Accordingly, the reference score may be a score set to determine whether or not to progress again the test of the second user.

The PC 101 may receive an input of reselecting the questions and the level of difficulty from the first user and create a data including the changed questions and level of difficulty (step 417).

The PC 101 may transmit the data having the reselected questions or level of difficulty to the virtual reality apparatus 102 (step 421).

The virtual reality apparatus 102 may progress a test on the basis of information on the questions for testing and the level of difficulty received from the PC 101. The virtual reality apparatus 102 may sense the eyeline, voice, gesture or the like of the second user using a sensor and a camera and create a second answer of the second user on the basis of a sensing result.

When the test is completed, the virtual reality apparatus 102 may transmit a data corresponding to the created answer to the PC 101 (step 425).

The PC 101 may receive a data corresponding to the created answer from the virtual reality apparatus 102 and mark the answer of the second user on the basis of the received data (step 427). The PC 101 may compare a marking result score with a reference score (step 415) and create and output a report on the basis of a compared result (step 419).

Figure 5:
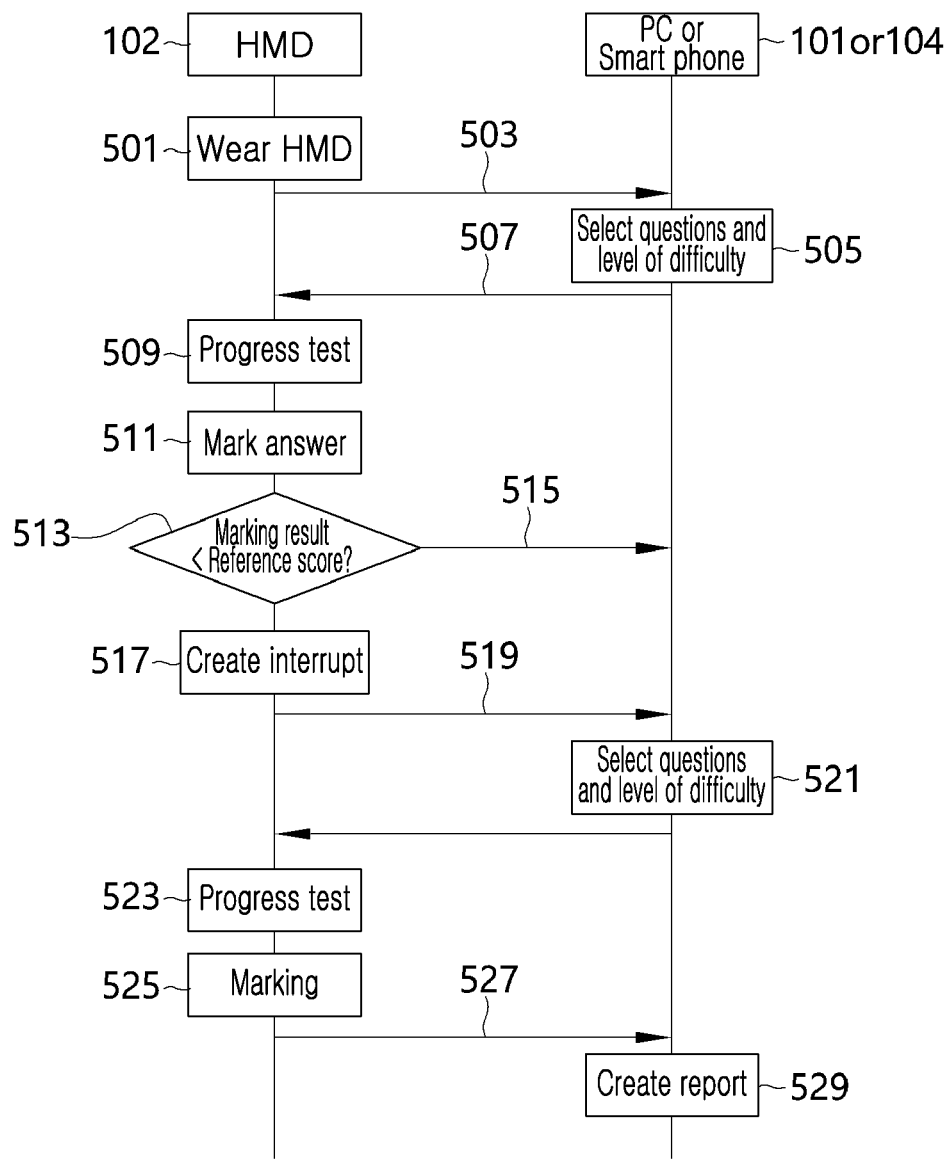
FIG. 5 is a flowchart illustrating the operation of a dementia diagnosis system according to another embodiment of the present invention.

FIG. 5 is a flowchart illustrating the operation of a dementia diagnosis system according to another embodiment of the present invention, and unlike the example shown in FIG. 4, it may be configured such that the virtual reality apparatus 102 itself marks the answers selected by the second user and transmits a marking result to the PC 101. In addition, the virtual reality apparatus 102 may create an interrupt for readjusting the questions or the level of difficulty by comparing a marking result score with a reference score and transmit the created interrupt to the PC 101.

The virtual reality apparatus 102 may sense wearing of the virtual reality apparatus 102 by the second user (step 501).

If wearing of the virtual reality apparatus 102 by the second user is sensed, the virtual reality apparatus 102 may create a sensing signal on the basis of the sensed result and transmit the created sensing signal to the PC 101 (step 503).

The PC 101 may output a screen in response to the sensing signal received from the virtual reality apparatus 102 so that the first user may recognize that the second user wears the virtual reality apparatus 102. The PC 101 may output a user interface for requesting input of contents for diagnosing dementia of the second user in response to the sensing signal. The PC 101 may receive an input for selecting questions mapped to the contents and a level of difficulty from the first user through the user interface (step 505).

The PC 101 may transmit questions for testing and a level of difficulty to the virtual reality apparatus 102 on the basis of the information selected by the first user (step 507).

At this point, the PC 101 may also transmit data corresponding to the correct answers of the questions, together with the questions for testing, to the virtual reality apparatus 102. For example, the questions for testing may be questions included in at least one among attentiveness contents 130a, visuospatial ability contents 130b, memory retention ability contents 130c, execution ability contents 130d, language ability contents 130e, calculation ability contents 130f, sound cognition ability contents 130g, and the user information storage unit 130h stored in the memory of the PC 101.

The virtual reality apparatus 102 may progress a test on the basis of the questions for testing and the level of difficulty received from the PC 101 (step 509). The virtual reality apparatus 102 may sense the eyeline, voice, gesture or the like of the second user using a sensor and a camera and create an answer of the second user on the basis of a sensing result.

The virtual reality apparatus 102 may mark the created answer of the second user (step 511).

The virtual reality apparatus 102 may compare a marking result score with a reference score (step 513) and transmit a data based on a compared result to the PC 101 (step 515).

The PC 101 may create a report on the basis of the marking result received from the virtual reality apparatus 102 (step 529).

Additionally, when the test result score is lower than the reference score, the virtual reality apparatus 102 may create an interrupt for requesting reselection of the questions and the level of difficulty of the questions and transmit the interrupt to the PC 101 (steps 517 and 519). This is to readjust the questions and the level of difficulty to correctly diagnose dementia when the test result score of the second user is extremely low. Accordingly, the reference score may be a score set to determine whether or not to progress again the test of the second user.

The PC 101 may output a screen requesting reselection of the questions and the level of difficulty of the questions in response to the interrupt provided by the virtual reality apparatus 102.

The PC 101 may receive an input of reselecting the questions and the level of difficulty from the first user and create a data including the changed questions and level of difficulty (steps 521 and 523).

The virtual reality apparatus 102 may progress a test on the basis of the questions for testing and the level of difficulty received from the PC 101 (step 523). The virtual reality apparatus 102 may sense the eyeline, voice, gesture or the like of the second user using a sensor and a camera and create an answer of the second user on the basis of a sensing result.

The virtual reality apparatus 102 may mark the created answer of the second user (step 525).

The virtual reality apparatus 102 may compare a marking result score with a reference score (step 513) and transmit a data based on a compared result to the PC 101 (step 527).

The PC 101 may create a report on the basis of the marking result received from the virtual reality apparatus 102 (step 529).

As shown in each embodiment described above, the virtual reality apparatus 102 may transmit various kinds of information related to the test progressed using a virtual reality image, such as whether a user wears the virtual reality apparatus, information sensed through various sensors such as the eyeline, voice, gesture or the like of the user, answers of the second user created on the basis of the sensed information, and a result of marking the answers of the second user, to an external device connected to the virtual reality apparatus 102, such as a PC or a smart phone, in real-time or at a specific time point.

Figure 6:
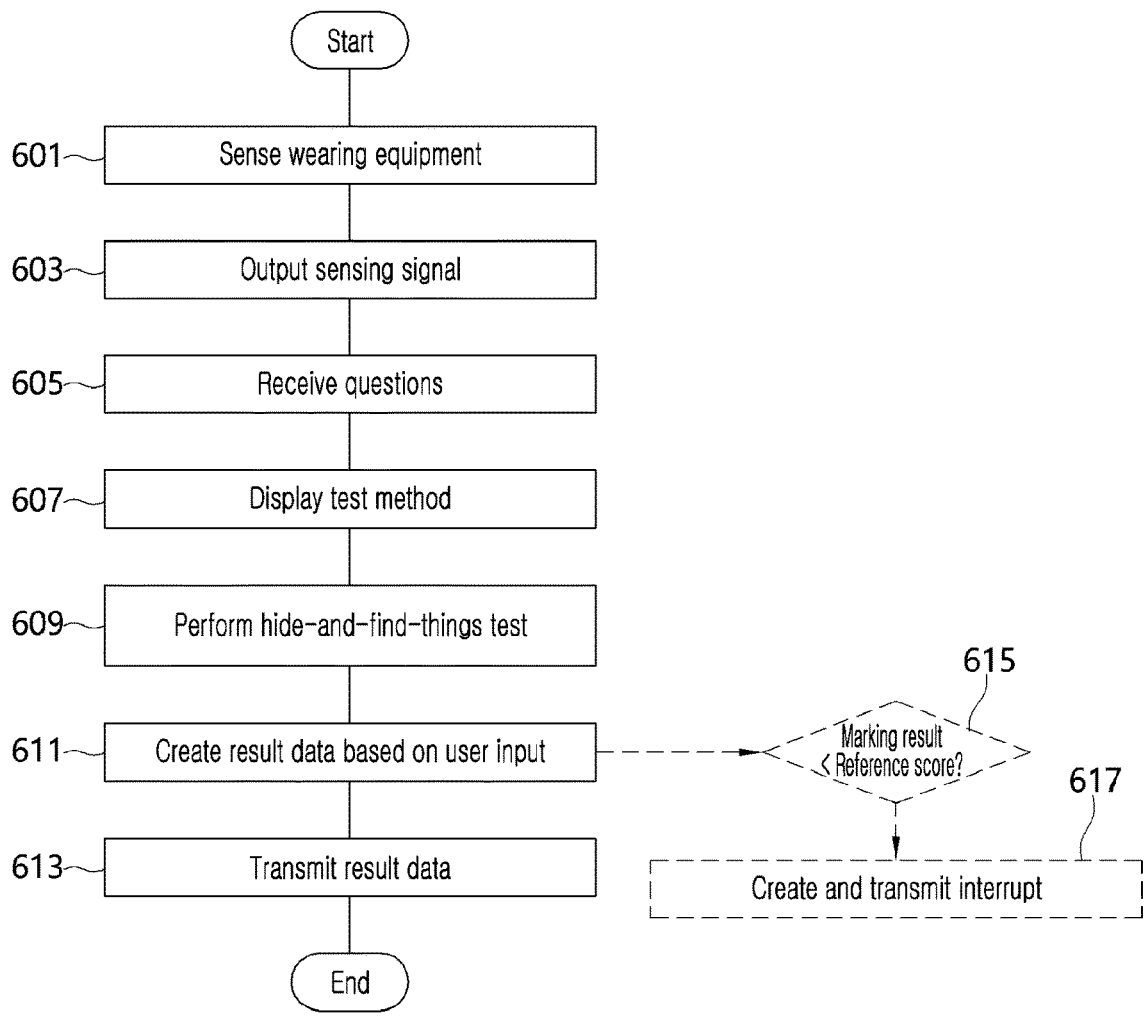
FIG. 6 is a flowchart illustrating the operation of a virtual reality apparatus according to an embodiment of the present invention.

FIG. 6 is a flowchart illustrating the operation of a virtual reality apparatus 102 according to an embodiment of the present invention, and FIGS. 7 to 12 are views showing an example for describing a method of diagnosing dementia by progressing a hide-and-find-things test using a dementia diagnosis system 100 according to the present invention.

Figure 7:
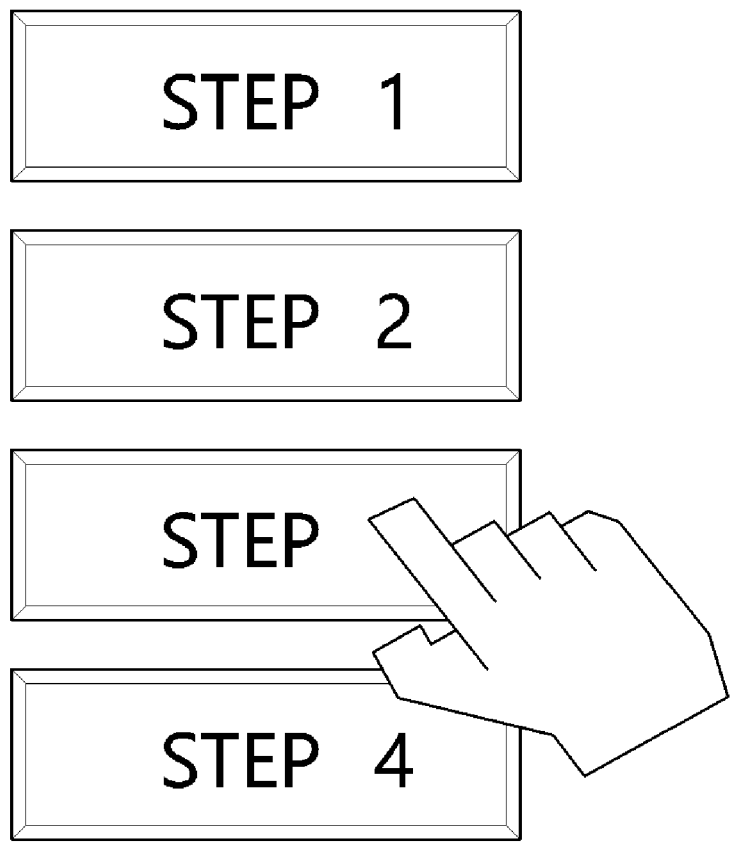
FIGS. 7 to 12 are views showing an example for describing a method of diagnosing dementia by progressing a hide-and-find-things test using a dementia diagnosis system of the present invention.

Referring to FIGS. 6 and 7, the virtual reality apparatus 102 may sense wearing of the virtual reality apparatus 102 by the second user at step 601.

If wearing of the virtual reality apparatus 102 by the second user is sensed, the virtual reality apparatus 102 may create a sensing signal on the basis of the sensed result and transmit the created sensing signal to the PC 101 (step 603).

As shown in FIG. 7, the PC 101 may output a guidance screen in response to the sensing signal received from the virtual reality apparatus 102 so that the first user may recognize that the second user wears the virtual reality apparatus 102. The PC 101 may output a user interface for requesting input of contents for diagnosing dementia of the second user in response to the sensing signal. The PC 101 may receive an input for selecting questions mapped to the contents and a level of difficulty from the first user through the user interface.

As a specific example, the level of difficulty may be divided into four levels capable of hiding 2 to 32 items or nine levels capable of hiding 2 to 32 items.

Figure 8:

Referring to FIGS. 6 and 8, the virtual reality apparatus 102 may receive the questions for testing and information on the level of difficulty at step 605. The virtual reality apparatus 102 may output a screen explaining a method of progressing a test on the basis of the received questions for testing and information on the level of difficulty. For example, as shown in FIG. 8, the screen explaining a method of progressing a test may have a room 801 as a background in a virtual reality space and include an avatar 810 which explains the test method.

The avatar 810 may explain the method of progressing a test in the form of visual information and sound information. For example, the avatar may output a voice message such as "From now, I'll show you an item and hide it. Guess where I hide the Teddy bear."

Figure 9:
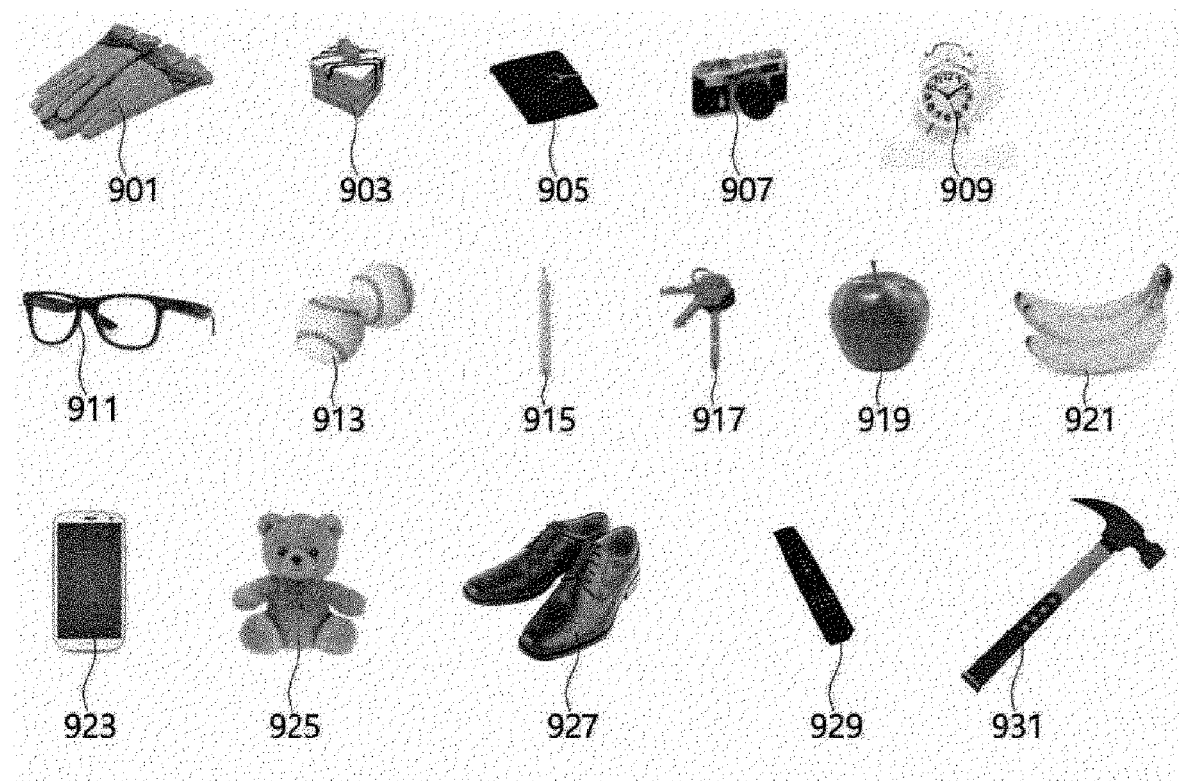

Referring to FIGS. 6 and 9, the virtual reality apparatus 102 may perform a test at step 609 when explaining the test method is finished.

The virtual reality apparatus 102 may sense the eyeline, voice, gesture or the like of the second user using a sensor and a camera and create an answer of the second user on the basis of a sensing result. When the test is progressed, the avatar 810 may appear and show a plurality of items in order and hide the items in various places in the room 801 displayed as a background.

As shown in FIG. 9, the items hidden by the avatar 810 may be at least some items selected among a glove 901, a cake 903, a wallet 905, a camera 907, a watch 909, glasses 911, a baseball 913, a candle 915, a key 917, an apple 919, a banana 921, a cellular phone 923, a Teddy bear 925, a shoe 927, a remote controller 929, and a hammer 931. However, it should be noted that in the present invention, the items hidden by the avatar 810 are not limited to the items shown in FIG. 9 and may be a person or an animal.

The room displayed as a background may be configured in the form of a comfortable personal space, and the places for hiding items and the number of items may be freely adjusted as the level of difficulty is adjusted.

In addition, frequently used items may be selected from a Frequency Dictionary of Korean, or the items may be selected among the items frequently used in everyday life.

Figure 10:
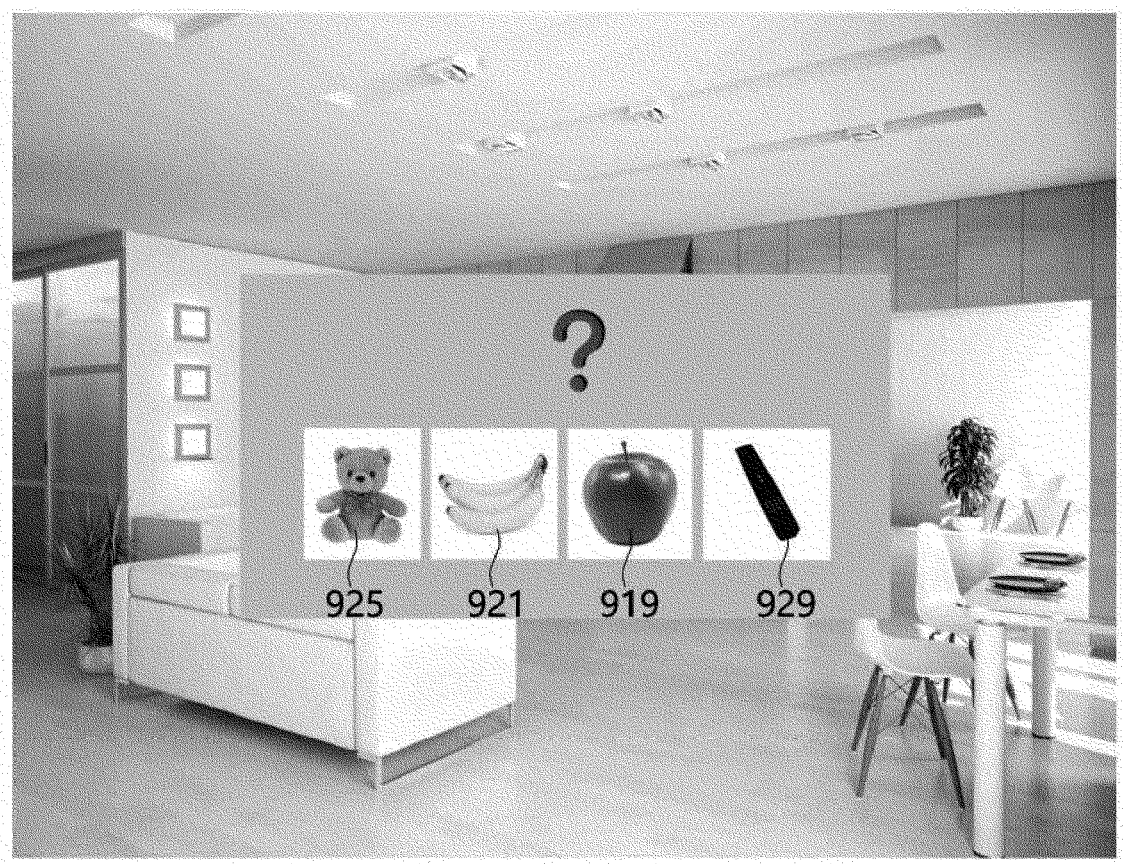

Referring to FIG. 10, once the items are hidden by the avatar 810, the virtual reality apparatus 102 may output an interface screen asking the second user to find the items. For example, the virtual reality apparatus 102 may output a question asking the second user to find out where the Teddy bear 925, the banana 921, the apple 919 or the remote controller 929 is hidden.

The virtual reality apparatus 102 may sense the eyeline, voice, gesture or the like of the second user using a sensor or a camera and move the eyeline of the second user and the location of the second user seen from the virtual reality space (e.g., the room 801) displayed as a background on the basis of the sensed result. Accordingly, the second user may control the eyeline and the location in the virtual reality space while wearing the virtual reality apparatus 102.

Figure 11:
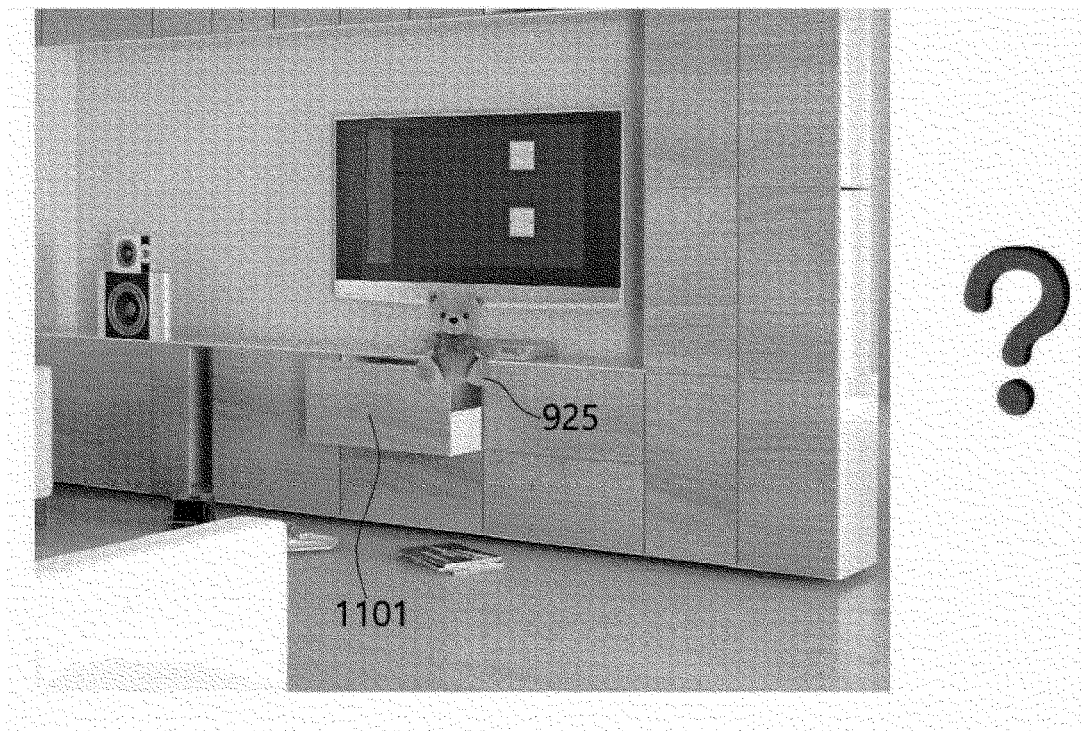

The example shown in FIG. 11 exemplarily shows a process in which the second user finds the Teddy bear 925 hidden by the avatar 810 in the drawer 1101.

Figure 12:
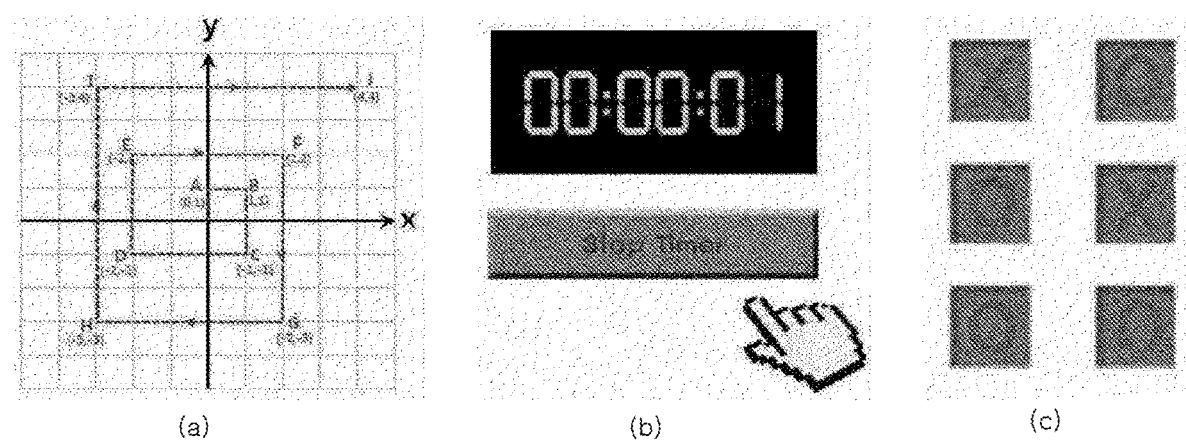

Referring to FIGS. 6 and 12, at step 611, the virtual reality apparatus 102 may create answers of the second user on the basis of the eyeline, voice, gesture or the like of the second user sensed while the second user progresses the test, and create a result data.

At this point, the result data created by the virtual reality apparatus 102 may include information on the distance that the second user has moved as shown in left of FIG. 12, information on the duration of time that the second user has participated in the test as shown in middle of FIG. 12, and information on the marking result, i.e., information on the answer sheet, as shown in right of FIG. 12, and the information may be individually displayed.

Meanwhile, it is preferable to set the test image properly. For example, the test image may be set to be played back for 6 or 7 minutes. This is since that if the playback time of the test image is too short, sufficient contents may not be included in the test image, and if the playback time is too long, the contents included in the test image are too much and thus it is difficult to correctly diagnose since the level of difficulty of the test abruptly increases.

At step 613, the virtual reality apparatus 102 may transmit the created test result to the PC 101 after the test is completed.

Meanwhile, a virtual reality apparatus 102 according to another embodiment of the present invention may progress marking by itself and transmit a marking result to the PC 101.

In addition, when the marking result score is lower than the reference score, the virtual reality apparatus 102 may output a screen requesting reselection of the questions and the level of difficulty of the questions. For example, at step 615, the virtual reality apparatus 102 may compare a marking result score with a reference score, create an interrupt for requesting reselection of the questions and the level of difficulty of the questions, and transmit the interrupt to the PC 101 when the test result score is lower than the reference score step (step 617).

FIGS. 13 to 23 are views showing an example describing another method of diagnosing dementia by progressing a hide-and-find-things test through a dementia diagnosis system 100 of the present invention.

Figures 13, 14:
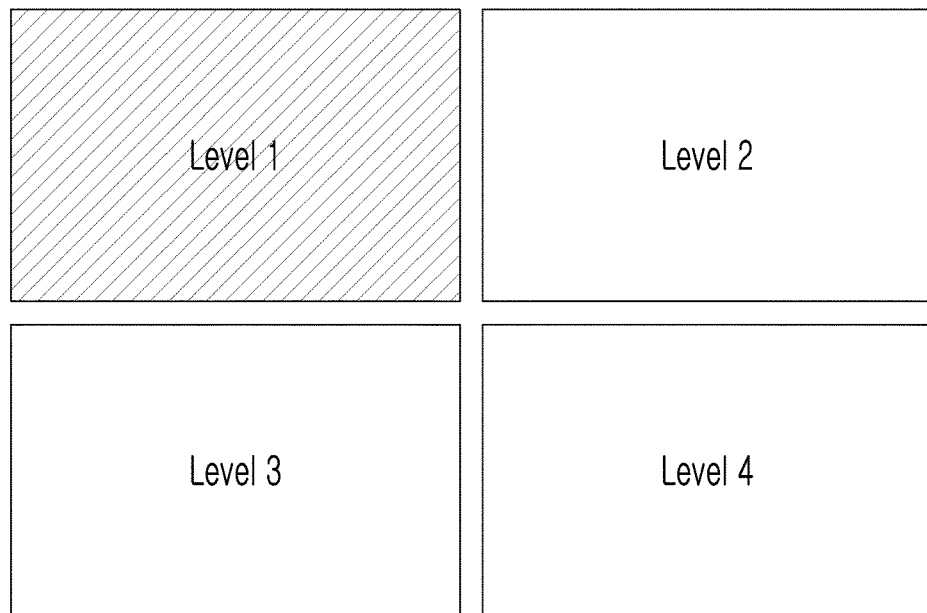

Referring to FIG. 13, before diagnosing dementia of the second user, the PC 101 may output a user interface for inputting basic information on the second user.

The user interface outputted from the PC 101, i.e., a basic information input screen, may include the name, sex, date of birth, age, education, handle, visual impairment, hearing disorder, test institute, test date, tester name, nationality, mother language, memorandum and the like of the second user (testee).

Referring to FIG. 14, the PC 101 may output a menu for setting a test level (level of difficulty of the test) in response to completion of the input of basic information by the first user.

The menu for setting a test level may be configured to select any one among, for example, a first level to a fourth level.

Figure 15:
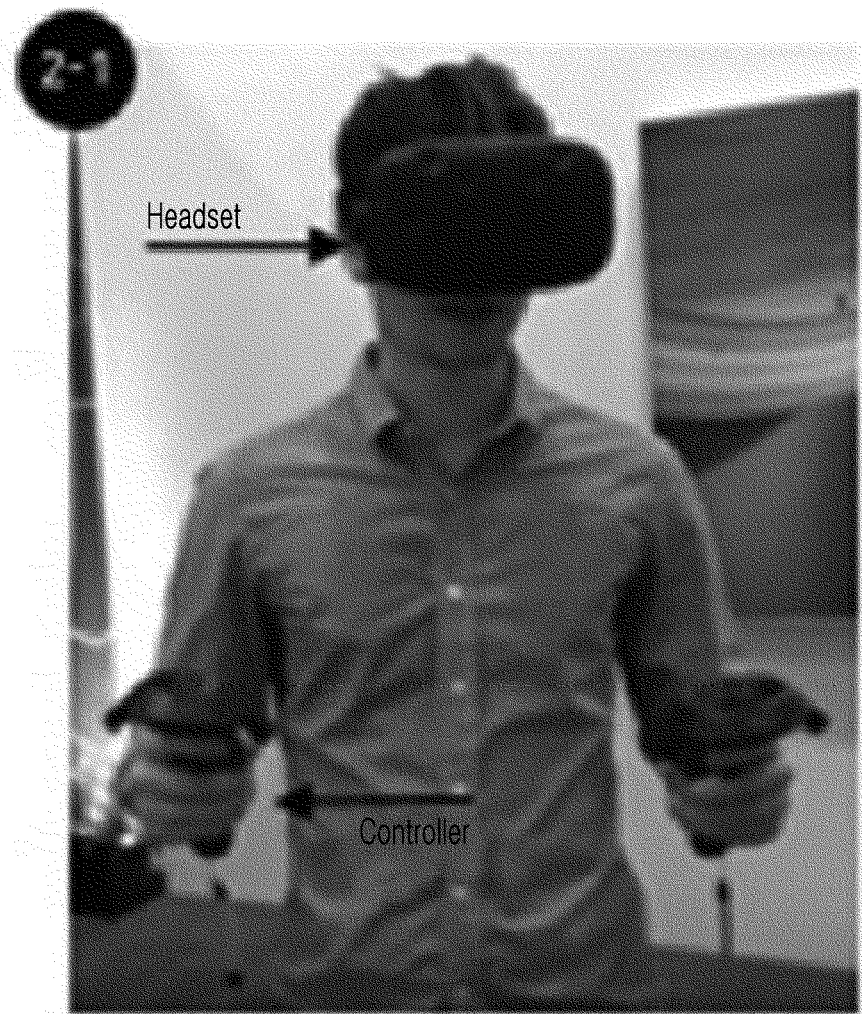

Referring to FIG. 15, when input of the basic information and setting of the test level are completed, the first user (tester) may guide to second user (testee) to wear the virtual reality apparatus 102. The first user may guide the second user to sit on a chair corresponding to the starting point of the test and explain how to use the virtual reality apparatus 102.

The virtual reality apparatus 102 may include a headset, such as a HMD, and a controller configured to be gripped in both hands. At this point, the first user may guide the second user to wear the headset to be aligned with both eyes and to hold the controller with both hands. In addition, the first user may confirm whether the second user correctly wears the virtual reality apparatus 102.

The confirmation method may include, for example, a process of confirming whether a lamp provided on one side of the headset is lit, a process of confirming whether a space is seen when the testee moves the head left and right, and a process of confirming whether a lamp provided in the controller held by both hands is lit. When all the confirmation processes are normally completed, the first user may remove the chair from the space and guide the second user to stand and wait at a corresponding point.

Figure 16:
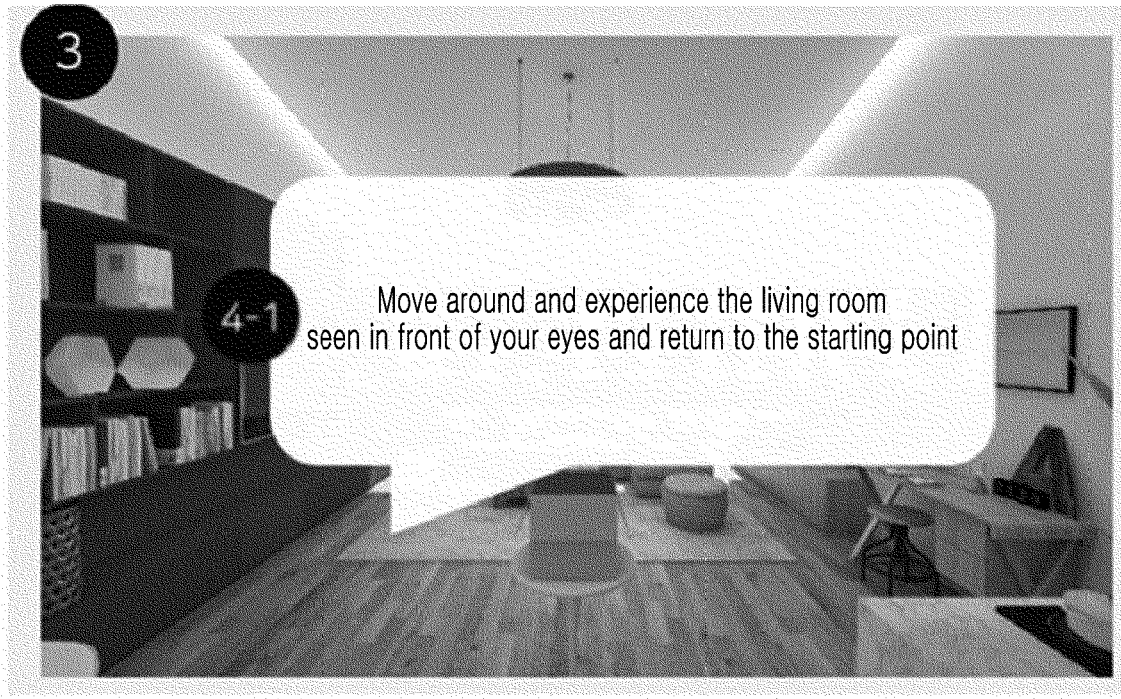

Referring to FIG. 16, the first user may control the PC 101 to direct start of the dementia test. The PC 101 may control the virtual reality apparatus 102 in response to the direction of the first user to start the dementia test. When the dementia test begins, the virtual reality apparatus 102 may output the screen as shown in FIG. 16.

For example, the virtual reality apparatus 102 may output a guidance message such as "Move around and experience the living room seen in front of your eyes and return to the starting point" so that the second user may recognize and learn the virtual reality space first. At this point, the guidance message may be any one among a character message, a voice and a combination of these.

When the guidance process is completed, the virtual reality apparatus 102 may perform a Practice trial process. The Practice trial process may include phrases such as "Move along the red line on the floor", "Open the drawer", "Take out the item in the drawer", "Put a sticker on the drawer", "Freely move around the living room, and look at the box while standing in the red circle", or the like. The virtual reality apparatus 102 may sequentially output the guidance phrases one by one and may output a new guidance phrase each time the second user completes an operation according to a corresponding guidance.

Figure 17:
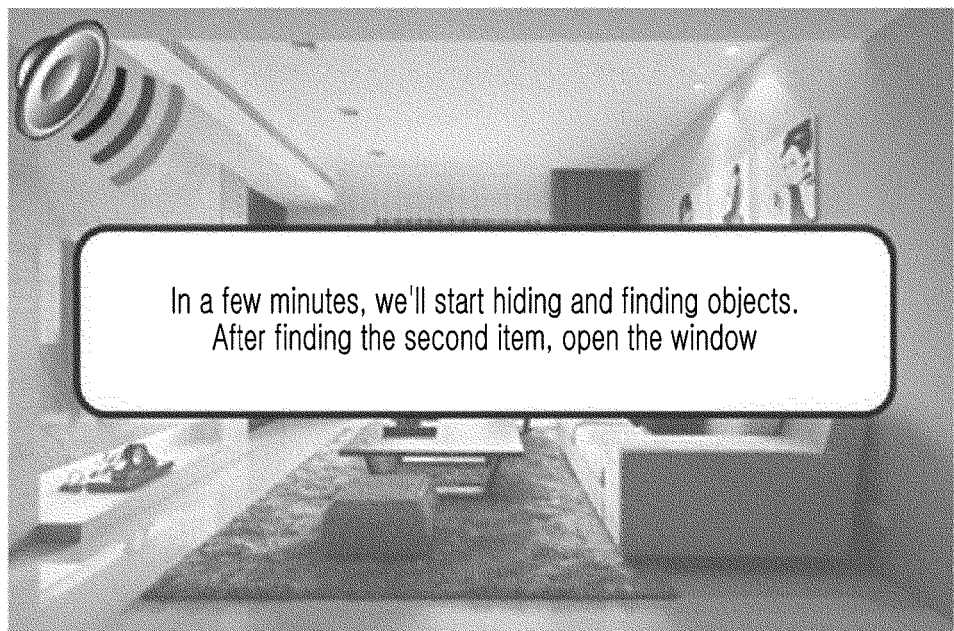

Referring to FIG. 17, the virtual reality apparatus 102 may perform a Prospective memory process when the Practice trial process is completed.

For example, in the Prospective memory process, the virtual reality apparatus 102 may output a guidance phrase such as "In a few minutes, we'll start hiding and finding objects. After finding the second item, open the window". The guidance phrase may also include a sentence such as "Turn off the heat of the pot after a while when you find all the items".

The reason of testing the Prospective memory after finding all the items in the Place-item matching process like this is to minimize the effect on the other assessments since if the Prospective memory is performed during the test, this may affect the time and distance.

Figure 18:

Referring to FIG. 18, when the Prospective memory process is completed, the virtual reality apparatus 102 may perform an object hiding process.

For example, in the object hiding process, the virtual reality apparatus 102 may output a guidance phrase such as "Check the item taken out from the box and remember where the item is hidden", or "Now, one item will be taken out and hidden in the space seen in front of you. Remember the item and the place where it is hidden."

In addition, the virtual reality apparatus 102 may output "apple", "banana" and the like as an example of a word corresponding to the hidden items.

According to an embodiment, in the object hiding process, the virtual reality apparatus 102 may output an image of a scenario of displaying an image of an item coming out and rotating 360 degrees, outputting a word matching the item as a voice signal, and hiding the item. Here, the reason of pronouncing a word is to confirm whether the user answers in the same way as answered in a scenario image shown before among a variety of names (e.g., a raw egg and a boiled egg) of the same item in the case of a free-recall assessment.

In addition, in the present invention, it may be configured only to show flying items rather than a human avatar coming out and hiding items, and the reason is that it is difficult to confirm how the items are hidden since the trajectory of the flying items is covered by a person, and adjustment of the flying speed of the items is limited since movement of the person should be controlled.

Figure 19A:

Referring to FIG. 19a, when the object hiding process is completed, the virtual reality apparatus 102 may perform an Item free-recall process. For example, in the Item free-recall process, the virtual reality apparatus 102 may output a guidance phrase such as "Tell as you remember the items that come out from the box" or "Now, tell as you remember all the items that are hidden just before".

Figures 19B, 20:

Meanwhile, the PC 101 may receive information on the items mentioned by the second user through the virtual reality apparatus 102 and output a screen for checking the answers of the second user as shown in FIG. 19*b* on the basis of the received information. Accordingly, the first user may recognize a result of the item free-recall test performed by the second user through the PC 101.

Referring to FIG. 20, when the Item free-recall process is completed, the virtual reality apparatus 102 may perform a Place free-recall process.

For example, in the Place free-recall process, the virtual reality apparatus 102 may output a phrase such as "Attach a sticker at a place where an item is hidden and return to the starting point" or "Move around the living room and attach a sticker at a place where an item is hidden". The reason of only attaching the sticker in the Place free-recall process is that if a user opens a drawer, it may affect the next performance of the Place-item matching process regardless of whether or not an item is in the drawer.

Figure 21:
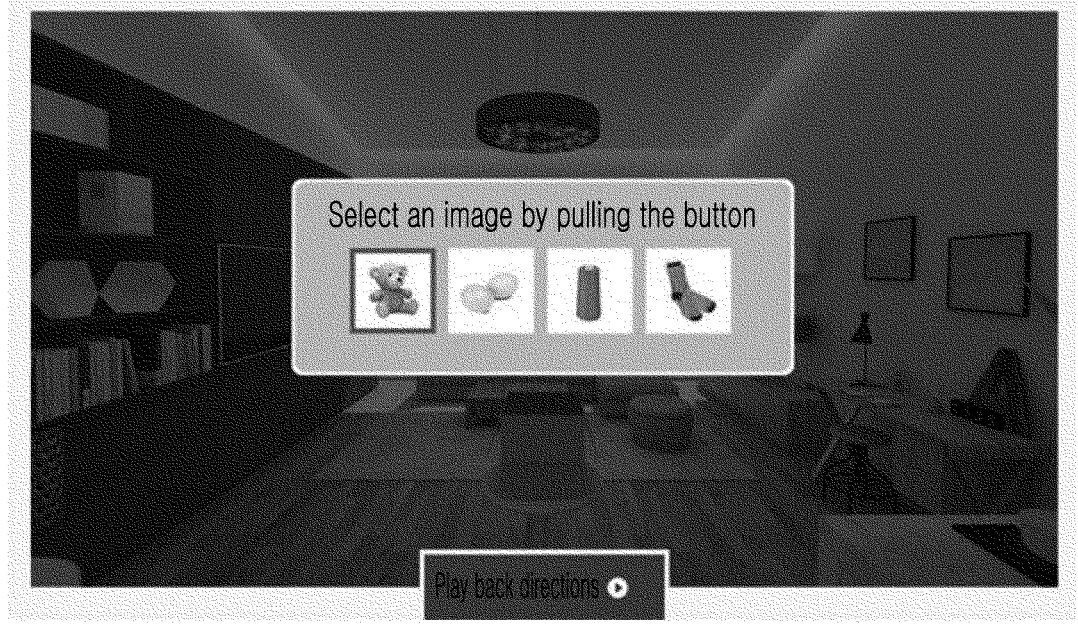

Referring to FIG. 21, when the Place free-recall process is completed, the virtual reality apparatus 102 may perform an Item recognition process.

For example, in the Item recognition process, the virtual reality apparatus 102 may output a phrase such as "Select an item hidden just before among the four items you're looking at". In the Item recognition process, the virtual reality apparatus 102 may display a plurality of items and output a scenario image asking the user to select at least one item among the items displayed in the previous screen.

Figure 22:
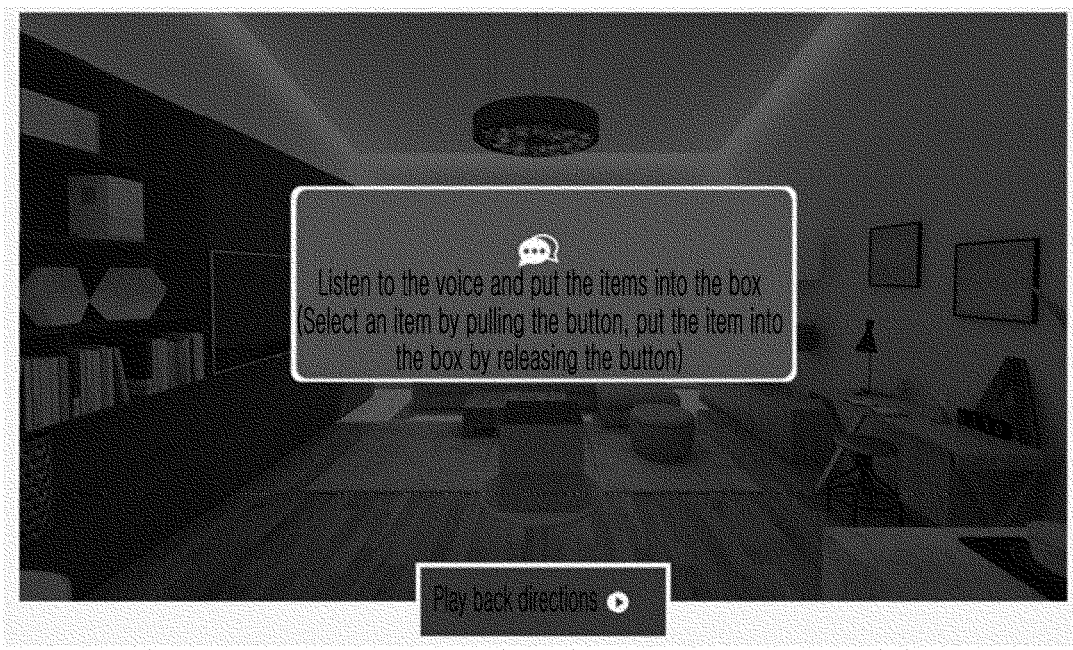

Referring to FIG. 22, when the Item recognition process is completed, the virtual reality apparatus 102 may perform a Place-item matching process.

For example, in the Place-item matching process, the virtual reality apparatus 102 may show a phrase such as "From now on, I will show you items one by one. Go to the places where the items are hidden and find and put them in a box. If you don't find anything you're looking for or there is something else, just come back." in the Place-item matching process.

According to an embodiment of the present invention, the dementia diagnosis system 100 calculates a score by dividing a situation into a case in which the second user successfully finds the items (O), a case in which the second user opens a place where other item is contained (Δ), and a case in which none of the items are found (X).

Here, since the case of opening a place where other item is contained (Δ) is helpful for finding next items and it is remembering that an item is hidden in a relevant place, this is reflected in calculating a score. Like this, since the present invention does not simply reflect only correct and incorrect answers in calculating a score in a hide-and-find-things test, but reflects various number of cases in calculating a score considering the case of opening a place where other item is contained (Δ), reliability of the test result can be enhanced.

When the Place-item matching process is completed finally, the dementia diagnosis system 100 may output a test result screen through the PC 101 as shown in FIG. 23.

As described above, the present invention can easily diagnose dementia using a computer and virtual reality equipment and reduce mental stress of a patient.

Although the present invention has been shown and described in relation to specific and preferred embodiments, it will be apparent to those skilled in the art that the present invention can be diversely modified and changed without departing from the technical features or field of the present invention provided by the claims described below.

The invention claimed is:

1. A virtual reality apparatus for providing a virtual reality environment based on an image, the apparatus comprising:
   a display for displaying the image;
   a sensor configured to sense motions of a user;
   circuitry configured to communicate with an external device, to display a virtual reality image on the display on the basis of questions for diagnosing a neurological disorder received from the external device, and to progress a test for diagnosing a neurological disorder while sensing motions of the user through the sensor; and
   a memory configured to store information on a standard wearing state which is a state of wearing the virtual reality apparatus at a predetermined position for the user to be provided with images, the information on the standard wearing state including feature values detected from the image of a body part acquired in the standard wearing state,
   wherein the questions for diagnosing a neurological disorder are presented through:
      a first screen for introducing at least one item and illustrating the at least one item being concealed inside a closeable receptacle at a particular location in a specific room in a virtual reality space such that the at least one item is out of sight from a vicinity of the at least one item unless the receptacle is opened; and
      a second screen including questions on the at least one item,
   wherein, when a dementia test result of the user is lower than a threshold value, the circuitry is configured to readjust a type and level of difficulty of the questions for the dementia test result based on an interrupt received from the external device,
   wherein the second screen is configured to perform all of the following steps in a listed order:
      a recall step of diagnosing whether a user remembers the at least one item which is concealed inside the receptacle;
      a recognition step of diagnosing whether the user distinguishes between the at least one item and other items; and
      a matching step of diagnosing whether the user can associate the at least one item inside the receptacle with the particular location,
   wherein the recall step includes an item free-recall process of inquiring the user to state as many of the at least one item as the user remembers, and a place free-recall process of attaching a marker on the receptacle where the at least one item is concealed and returning to a starting point, and
   wherein the second screen performing the matching step displays a virtual reality space in which the at least one item is concealed and includes a third user interface for asking the user to find the at least one item while the user himself or herself moves.

2. The apparatus according to claim 1, wherein the first screen is configured such that an avatar appears and conceals the at least one item in a specific space or specific furniture.

3. The apparatus according to claim 1, wherein background images of the first screen and the second screen are configured to be the same as a home interior environment in which the user lives.

4. The apparatus according to claim 1, wherein the questions for diagnosing a neurological disorder are classified into questions having any one level of difficulty among a plurality of levels of difficulty, and it is configured to increase the number of concealed items as the level of difficulty increases.

5. The apparatus according to claim 1, wherein the second screen performing the recall step sequentially displays the at least one item and includes a first user interface for inquiring the user to say where the at least one item is concealed as the at least one item is displayed concealed.

6. The apparatus according to claim 1, wherein the second screen performing the recognition step displays a package screen in which the at least one item and new items not introduced before are mixed and includes a second user interface for inquiring the user to distinguish between the at least one item and the new items in the package screen.

7. The apparatus according to claim 1, wherein the circuitry is further configured to calculate a score on the basis of a first condition of a distance that the user has moved, a second condition of a time consumed by the user to answer all the questions for diagnosing a neurological disorder, and a third condition of an answer sheet created on the basis of a voice or a motion of the user.

8. The apparatus according to claim 7, wherein the circuitry is further configured to calculate the score by assigning a preset weighting value to each of the first to third conditions.

9. The apparatus according to claim 7, wherein the circuitry is further configured to compare the calculated score with a reference score and determines the second user as normal if the calculated score is equal to or higher than the reference score.

10. The apparatus according to claim 7, wherein the result processing module transmits the calculated score to the external device.

11. The apparatus according to claim 1, further including a wireless communication module or a wired communication module, and the external device is a smart phone or a PC.

12. A method of driving the virtual reality apparatus of claim 1, the method comprising:
receiving the questions for diagnosing a neurological disorder from the external device;
displaying the virtual reality image through the display on the basis of questions for diagnosing a neurological disorder, and progressing a test using the virtual reality image according to a motion of the user sensed through the sensor; and
transmitting information related to the test progressed using the virtual reality image to the external device, wherein the displaying of a virtual reality image includes:
displaying the first screen for concealing at least an item at a particular location inside the receptacle in the virtual reality space after introducing the item; and
displaying the second screen including questions on the at least an item.

13. The method according to claim 12, wherein the first screen is configured such that an avatar appears and conceals the at least an item in a specific space or specific furniture.

14. The method according to claim 13, wherein background images of the first screen and the second screen are configured to be the same as a home interior environment in which the user lives.

15. The method according to claim 12, wherein the questions for diagnosing a neurological disorder are classified into questions having any one level of difficulty among a plurality of levels of difficulty, and it is configured to increase the number of concealed items as the level of difficulty increases.

16. The method according to claim 12, wherein the recall step includes:
sequentially displaying the concealed items; and
providing a first user interface for inquiring the user to say where the displayed items are concealed.

17. The method according to claim 12, wherein the recognition step includes:
displaying a package screen in which the concealed items and new items not introduced before are mixed; and
providing a second user interface for inquiring the user to distinguish between the concealed items and the new items in the package screen.

18. The method according to claim 12, further comprising calculating a score on the basis of a first condition of a distance that the user has moved, a second condition of a time consumed by the user to answer all the questions for diagnosing dementia, and a third condition of an answer sheet created on the basis of a voice or a motion of the user.

19. The method according to claim 18, wherein calculating a score calculates the score by assigning a preset weighting value to each of the first to third conditions.

20. The method according to claim 18, further comprising:
comparing the calculated score with a reference score; and
determining the second user as normal if the calculated score is equal to or higher than the reference score.

* * * * *